United States Patent
Harjes et al.

(10) Patent No.: US 8,388,892 B2
(45) Date of Patent: Mar. 5, 2013

(54) IN-LINE LOSS-ON-IGNITION MEASUREMENT SYSTEM AND METHOD

(75) Inventors: Daniel Harjes, Allston, MA (US); John Williams, Lexington, MA (US); James A. Bickford, Winchester, MA (US); Daniel Traviglia, Allston, MA (US); David G. D'Amore, Winthrop, MA (US); James D. Derouin, Taunton, MA (US)

(73) Assignee: The Charles Stark Draper Laboratory, Inc., Cambridge, MA (US)

( * ) Notice: Subject to any disclaimer, the term of this patent is extended or adjusted under 35 U.S.C. 154(b) by 49 days.

(21) Appl. No.: 12/927,364

(22) Filed: Nov. 12, 2010

(65) Prior Publication Data

US 2011/0066286 A1 Mar. 17, 2011

Related U.S. Application Data

(63) Continuation-in-part of application No. 12/657,706, filed on Jan. 26, 2010, now abandoned.

(60) Provisional application No. 61/205,961, filed on Jan. 26, 2009.

(51) Int. Cl.
| | |
|---|---|
| G01N 31/12 | (2006.01) |
| G01N 21/72 | (2006.01) |
| G01N 1/18 | (2006.01) |
| G01M 1/38 | (2006.01) |
| G05B 13/00 | (2006.01) |
| G05B 15/00 | (2006.01) |
| G05D 23/00 | (2006.01) |
| G01N 31/00 | (2006.01) |

(52) U.S. Cl. .......... 422/78; 436/155; 436/157; 700/274; 702/24

(58) Field of Classification Search ........................ None
See application file for complete search history.

(56) References Cited

U.S. PATENT DOCUMENTS

| | | | | |
|---|---|---|---|---|
| 4,518,699 | A | * | 5/1985 | Bohl ............................ 436/49 |
| 4,787,052 | A |   | 11/1988 | Yamaguchi |
| 4,846,292 | A | * | 7/1989 | Narukawa ..................... 177/50 |
| 5,173,662 | A | * | 12/1992 | Trerice et al. ................ 324/642 |
| 5,186,522 | A |   | 2/1993 | Spencer et al. |
| 2005/0048661 | A1 |   | 3/2005 | Droit et al. |
| 2005/0213633 | A1 | * | 9/2005 | Burian et al. .................. 374/27 |
| 2010/0198408 | A1 |   | 8/2010 | Harjes et al. |

FOREIGN PATENT DOCUMENTS

| | | | |
|---|---|---|---|
| CN | 1920524 A | * | 2/2007 |
| WO | WO 2010133715 A1 | * | 11/2010 |

OTHER PUBLICATIONS

Certified translation of CN-1920524-A.*
International Searching Authority, Written Opinion of the International Searching Authority for International Application No. PCT/US2011/001287, 7 pages (unnumbered), Dec. 8, 2011.

* cited by examiner

Primary Examiner — Jill Warden
Assistant Examiner — Charles D Hammond
(74) Attorney, Agent, or Firm — Lando & Anastasi, LLP

(57) ABSTRACT

An in-line loss-on-ignition measurement system includes an on-site extractor subsystem configured to collect fuel or a combustion by-product from a hydrocarbon fuel burning plant. An on-site analyzer is configured to receive the collected matter from the extractor subsystem and configured to weigh the collected matter, burn the collected matter, and weight the collected matter again. A controller is responsive to the analyzer and is configured to determine the loss-on-ignition data for the plant based on the weight of the collected matter before and after it is burned in the analyzer.

11 Claims, 17 Drawing Sheets

IN-LINE LOSS-ON-IGNITION MEASUREMENT SYSTEM AND METHOD

RELATED APPLICATIONS

This application is a continuation-in-part application of U.S. patent application Ser. No. 12/657,706, filed Jan. 26, 2010 now abandoned which claims the claims the benefit of and priority to U.S. Provisional Application Ser. No. 61/205,961, filed on Jan. 26, 2009 under 35 U.S.C. §§119, 120, 363, 365, and 37 C.F.R. §1.55 and §1.78.

FIELD OF THE INVENTION

The subject invention relates to hydrocarbon (e.g., coal) burning plants and a system and method for measuring loss-on-ignition of such plants.

BACKGROUND OF THE INVENTION

In industrial generators, hydrocarbon fuel, such as coal is burned to create steam used to drive turbine generators. For a combustor to operate efficiently and to produce an acceptably complete combustion that generates bi-products falling within the limits imposed by environmental regulations and design constraints, all of the individual burners in the combustor must operate cleanly and efficiently and all post-combustion systems must be properly balanced and adjusted. Emissions of unburned carbon (i.e., loss-on-ignition (LOI) data), NOx, carbon monoxide and/or other bi-products are generally monitored to ensure compliance with environmental regulations and to ensure compliance with design constraints. See U.S. Pat. No. 6,389,330 incorporated herein by this reference.

As stated in the '330 patent, some emissions, such as the concentration of unburned carbon in fly-ash, are difficult to monitor on-line and continuously. In most cases, these emissions are measured on a periodic or occasional basis by extracting a sample of ash and sending a sample to a laboratory for analysis. Usually the sample of fly-ash is sent to an offsite lab where the sample is weighed, burned, and reweighed. The analysis may take days to a week or more. Most power plants do not have a chemical lab on-site and, due to the elapsed time for an analysis, the plant efficiency is frequently not at an optimum level. The '330 patent proposes monitoring the radiation emitted from a post-flame zone of the combustor and in response to a fluctuation component of the radiation and then calculating one or more combustion parameters.

The RCA 2000 residual carbon analyzer (M&W Asketeknik) is advertised to extract fly-ash from the flue gas via a cyclone and analyze it in a transducer using light. The result of the analysis is sent to the control room. See also U.S. Pat. Nos. 5,774,176 and 5,173,662 incorporated herein by this reference.

Still, it appears no prior system is able to measure loss-on-ignition (LOI) directly, on-site, continuously, automatically (e.g., without the need for operator intervention) and without the need for calibration.

BRIEF SUMMARY OF THE INVENTION

It is therefore an object of this invention to provide a new loss-on-ignition measurement system and method. Such a system and method, in one preferred embodiment, is able to measure loss-on-ignition directly and is able to measure loss-on-ignition on-site in a continuous and automatic fashion without the need for extensive calibration. It is a further object of this invention to provide such a system and method which, in one example, is self-cleaning.

The subject invention, however, in other embodiments, need not achieve all these objectives and the claims hereof should not be limited to structures or methods capable of achieving these objectives.

This invention features, in one aspect, an in-line loss-on-ignition measurement system. An on-site extractor subsystem is configured to collect fuel or a combustion by-product from a hydrocarbon fuel burning plant. An on-site analyzer is configured to receive the collected matter from the extractor subsystem and to weigh the collected matter, burn the collected matter, and weight the collected matter again. A controller is responsive to the analyzer and is configured to determine the loss-on-ignition data for the plant based on the weight of the collected matter before and after it is burned in the analyzer.

One preferred extractor subsystems includes a cyclone device coupled to an exhaust stack of the plant and having an output connected to an input of the analyzer via one or more valves. A preferred analyzer includes an oven with a chamber therein, an opening in the chamber responsive to the extractor subsystem, a platen in the chamber for supporting the collected matter, a heater for the platen, and a balance for weighing the platen.

In one design, the heater is disposed within the platen. There may be a rod extending between the platen and the balance. The chamber preferably includes a purge inlet and a purge outlet for removing burned collected matter from the platen. The outlet can be connected to an exhaust stack of the plant. There may be a vacuum source between the purge outlet and the exhaust stack of the plant. The controller is preferably configured to read the weight of the collected matter on the platen, actuate the heater to burn the collected matter, read the weight of the burned collected matter on the platen, and purge the platen via the purge inlet and the purge outlet. The extractor subsystem may include a valve with an inlet receiving the collected matter and an outlet for dispensing the collected matter. The analyzer typically includes an oven with a sample inlet disposed beneath the valve outlet, the sample inlet connected to a chamber in the oven.

This invention also features an in-line loss-on-ignition measurement method. Fuel or a combustion by-product from a hydrocarbon fuel burning plant is extracted. The collected matter is weighed, burned, and weighed again. The loss-on-ignition data for the plant is based on the weight of the collected matter before and after it is burned.

The method may further include purging the collected matter after the second weighing. Preferably, the matter is purged back into an exhaust stack of the plant. Extracting may include removing ash and gas from an exhaust stack of the plant, delivering the ash to an analyzer and then back to the stack, and delivering the gas back to the stack. One or more gas sensors may be used to analyze the gas before it is delivered back to the stack.

BRIEF DESCRIPTION OF THE SEVERAL VIEWS OF THE DRAWINGS

Other objects, features and advantages will occur to those skilled in the art from the following description of a preferred embodiment and the accompanying drawings, in which.

DETAILED DESCRIPTION OF THE INVENTION

Figure 1:
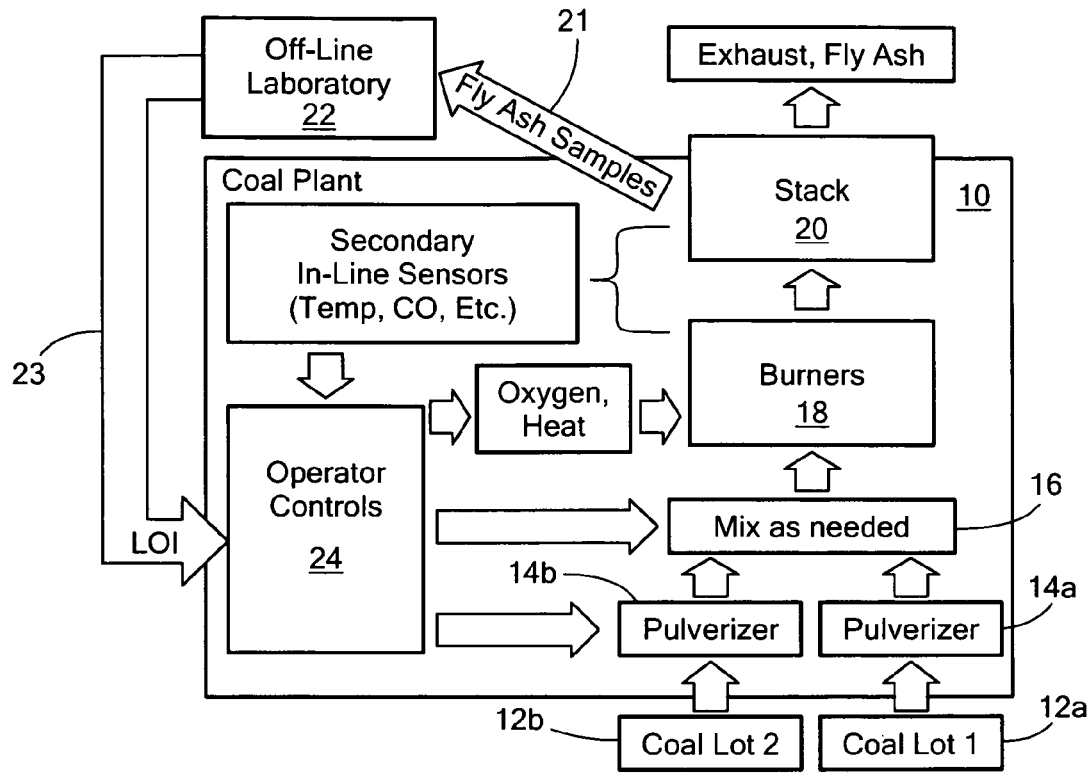
FIG. 1 is a block diagram depicting the primary components associated with a typical coal plant and the steps associated with one prior art method of determining loss-on-ignition.

Aside from the preferred embodiment or embodiments disclosed below, this invention is capable of other embodiments and of being practiced or being carried out in various ways. Thus, it is to be understood that the invention is not limited in its application to the details of construction and the arrangements of components set forth in the following description or illustrated in the drawings. If only one embodiment is described herein, the claims hereof are not to be limited to that embodiment. Moreover, the claims hereof are not to be read restrictively unless there is clear and convincing evidence manifesting a certain exclusion, restriction, or disclaimer.

One feature of the subject invention is the ability to measure loss-on-ignition in an automated fashion. Loss-on-ignition is the amount of coal that is not burned in a coal-fired power generation plant. Loss-on-ignition (LOI) typically changes from 2% to 20+%. If the LOI value can be measured in an automated fashion, then the amount of oxygen and coal fed into the furnace and pulverizers can be optimized resulting in higher efficiency, lower fuel cost, and reduced maintenance cost. For example, one energy generating complex burns about two-thousand tons of coal per day. If the yearly LOI were to be reduced from an average of 4% to an average of 3%, over seven-thousand tons of coal would be saved per year in just one plant. Not only would coal be saved, but emissions would be reduced and maintenance costs (per energy output) would be reduced.

The subject invention features an in-line system specifically tailored for rapid LOI sensing in coal and other hydrocarbon burning plants.

FIG. 1 depicts one prior method of determining loss-on-ignition of coal plant 10. Coal from lots 12a and 12b is pulverized by pulverizers 14a and 14b respectively, mixed (if desired) in mixers 16, and burned by burners 18. Fly-ash samples from stack 20 are collected as shown at 21 and sent to off-line laboratory 22 for analysis. Fly-ash is a combination of all solid matter exiting the coal plant burners. It contains both unburned coal (LOI) and mineral oxides generated from the impurities in each batch of coal. LOT data is then provided to an operator as shown at 23 who may use the various controls 24 to adjust, for example, the air to fuel ratio, and/or or the size of the fuel exiting pulverizers 14a, and 14b. As noted in the Background section above, the analysis process typically takes a few days to a week or more. Because of the elapsed time for analysis, plant efficiency is frequently not at an optimum level.

Figure 2:
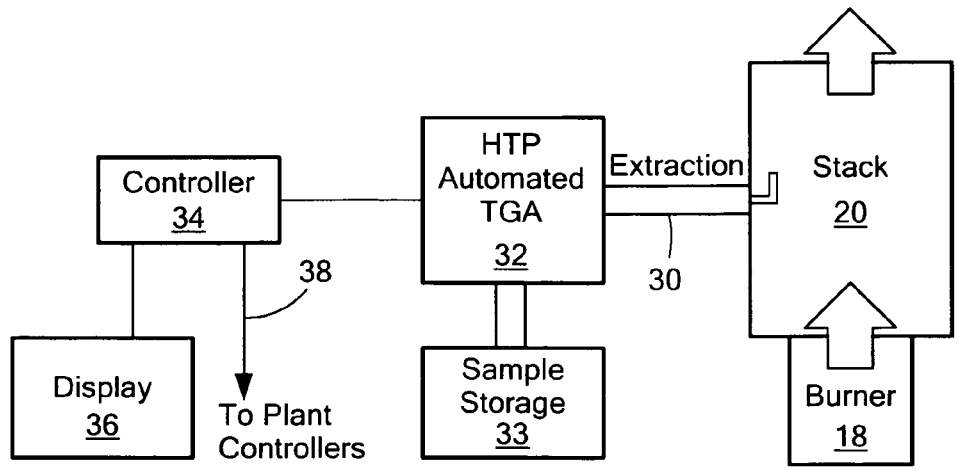
FIG. 2 is a highly schematic block diagram showing the primary components associated with a more automated system for and method of determining loss-on-ignition in accordance with an example of the invention.

In accordance with an example of the invention, the LOI data is determined on-site. Extractor 30, FIG. 2, in one example, is configured to collect fuel or, as shown in FIG. 2, a combustion by-product such as fly-ash from coal plant stack 20. In this example, analyzer 32 (e.g., an automatic thermal gravimetric analyzer) receives the fly-ash from the extractor and determines LOI data for the plant. Controller 34 is programmed to display the LOI data on display 36 (located, for example, in the control room of the plant) and/or to control, via electric signals as shown at 38, various plant parameters such as the air to fuel ratio or the size of the fuel exiting the pulverizers. Extracted samples, once analyzed, may be stored as shown at 33.

Figure 3:
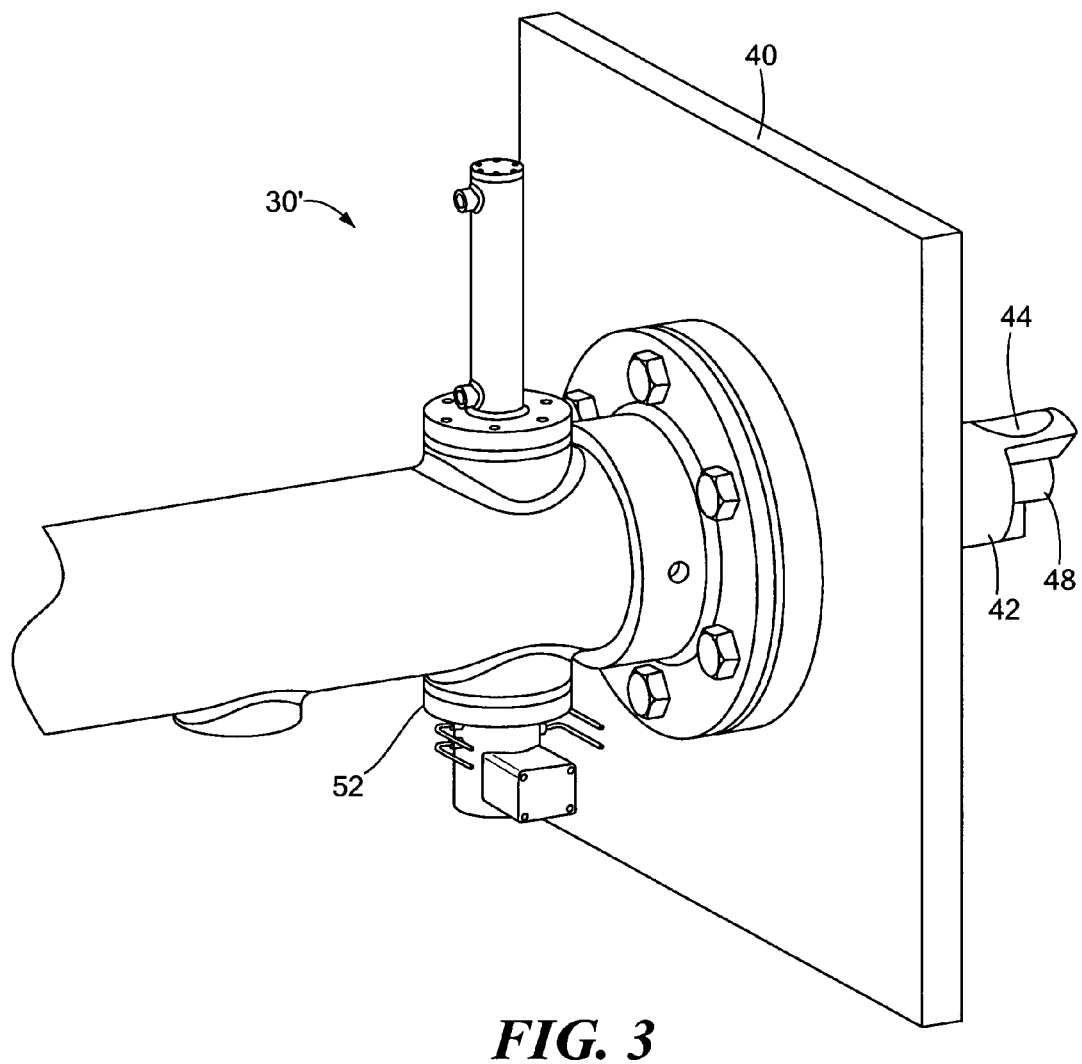
FIG. 3 is a schematic three-dimensional side view showing an example of a fly-ash extractor.

In one example, extractor 30', FIGS. 3-4 extends through stack wall 40 and includes cylinder 42 with catch funnel 44 within the stack and transverse through hole 46 outside of the stack. Moveable piston 48 within cylinder 42 includes collection volume orifice 50 transversely therethrough in communication with catch funnel 44 when piston 48 is extended into the position shown in FIG. 4A to receive fly-ash in the stack. Excess ash fills funnel 44 and prevents further build-up.

Figure 4A:
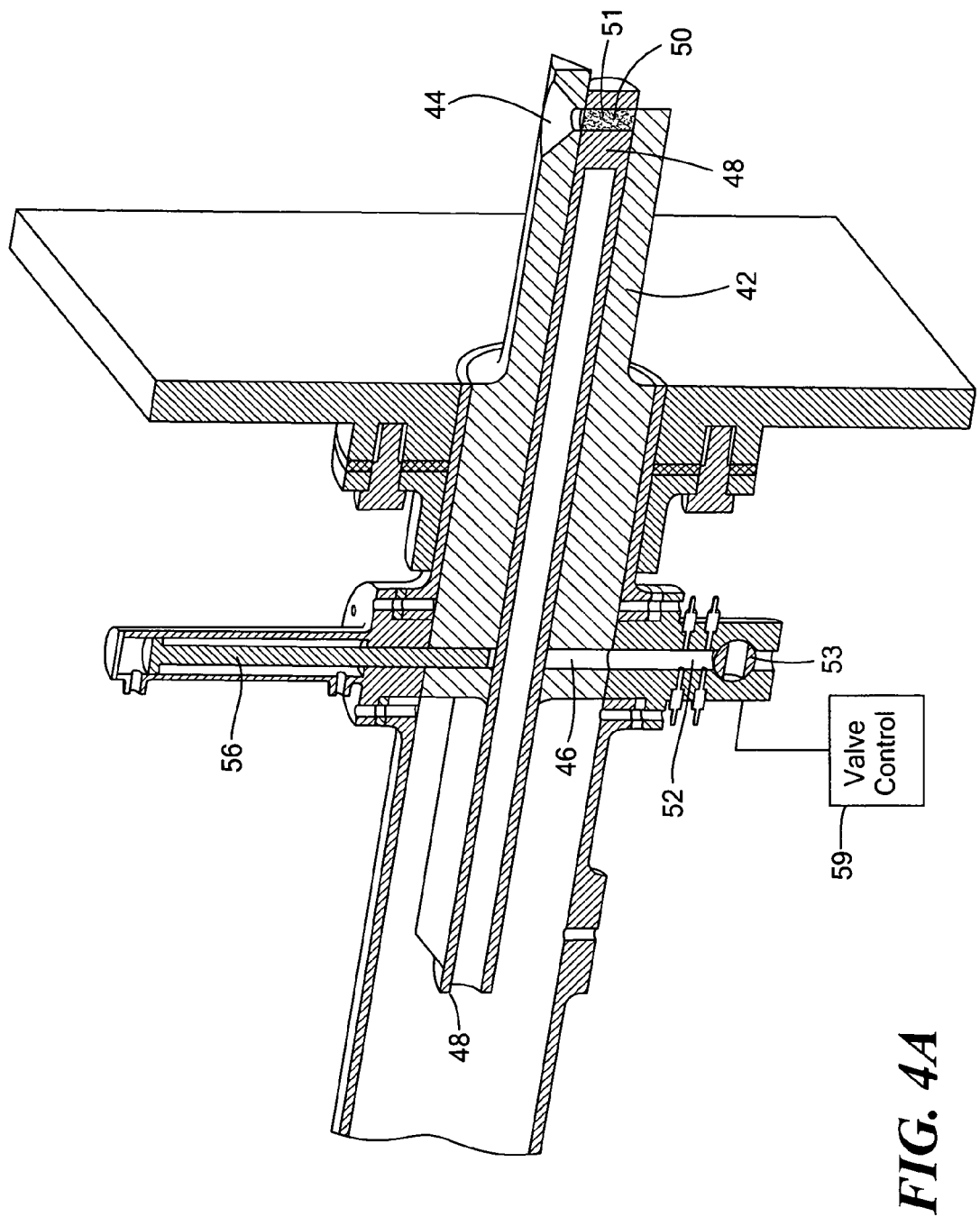
FIG. 4A-4F are schematic cross-sectional views of the fly-ash extractor of FIG. 3 in operation.
Figure 4B:
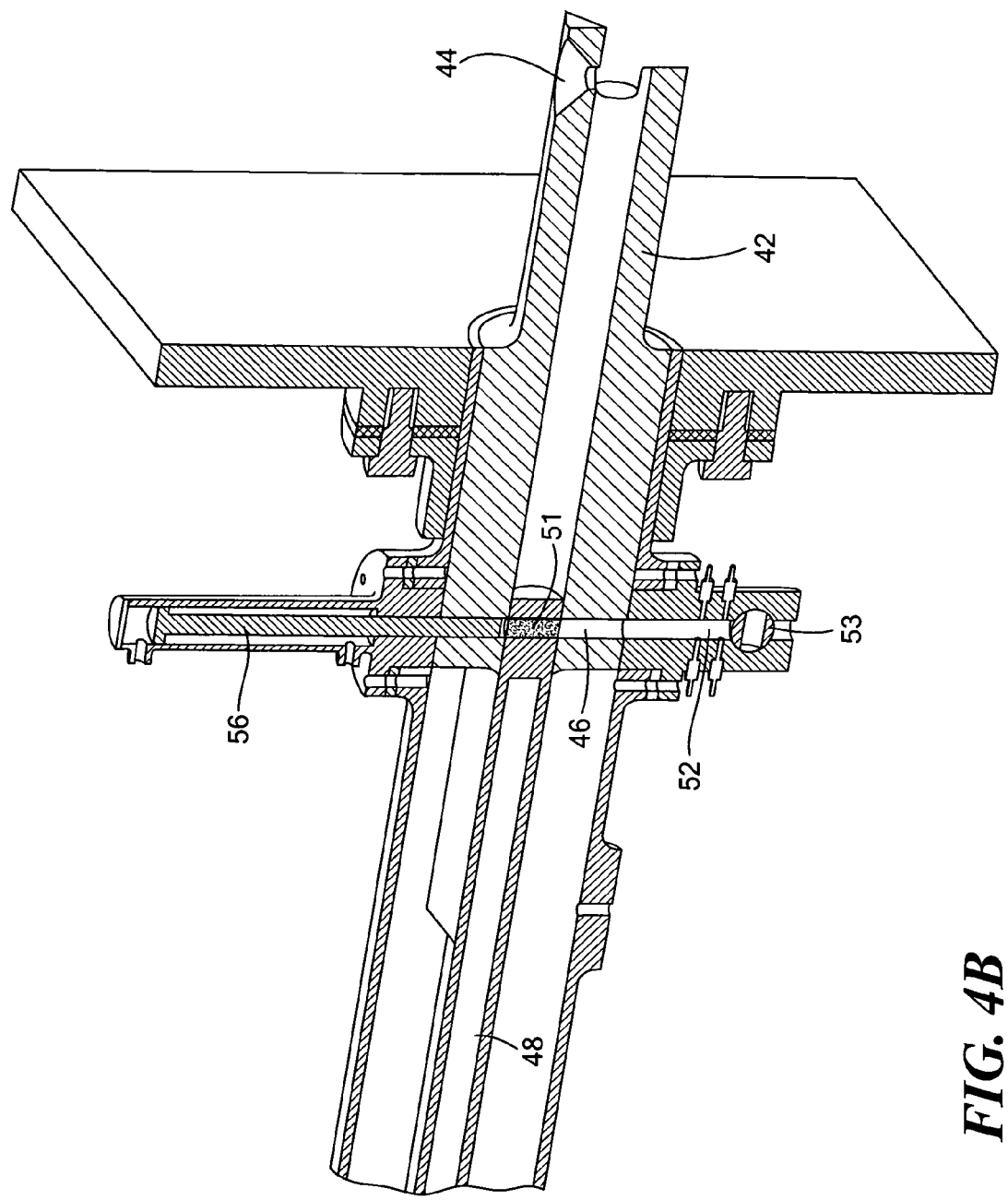
Figure 4C:
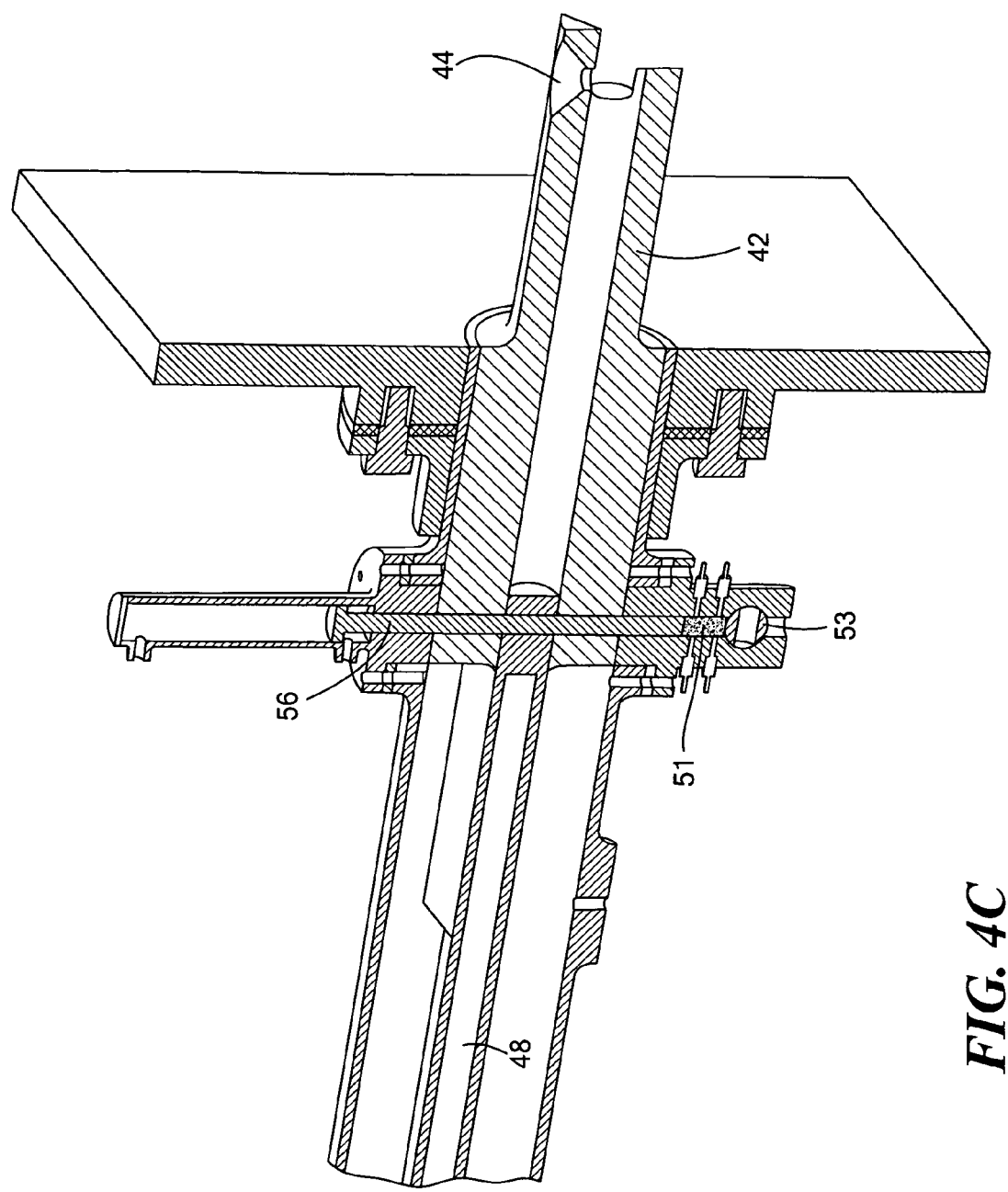
Figure 4D:
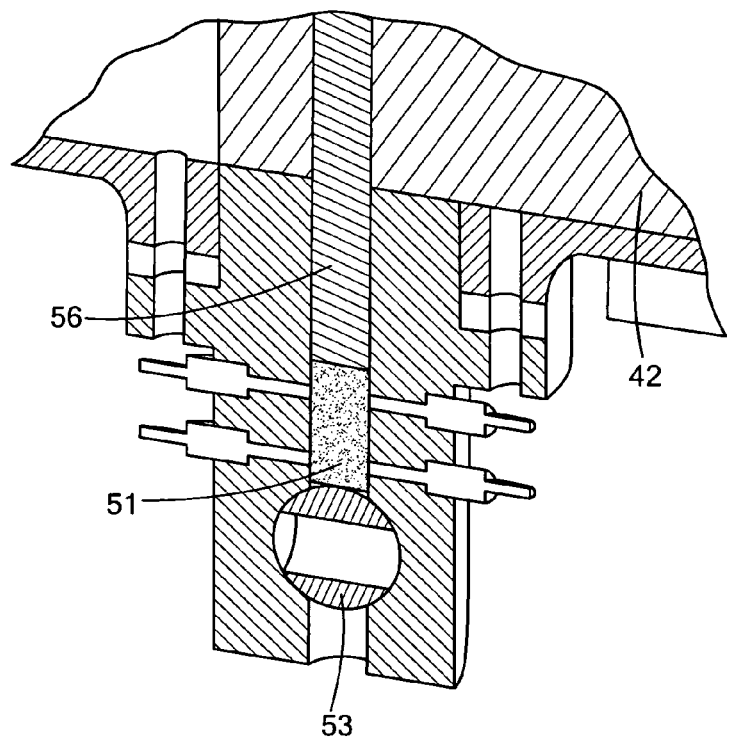
Figure 4E:
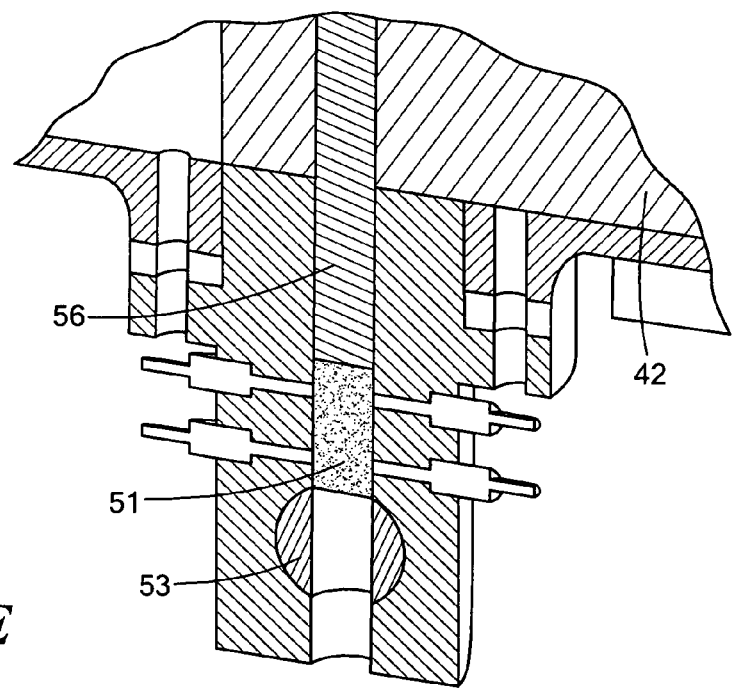
Figure 4F:
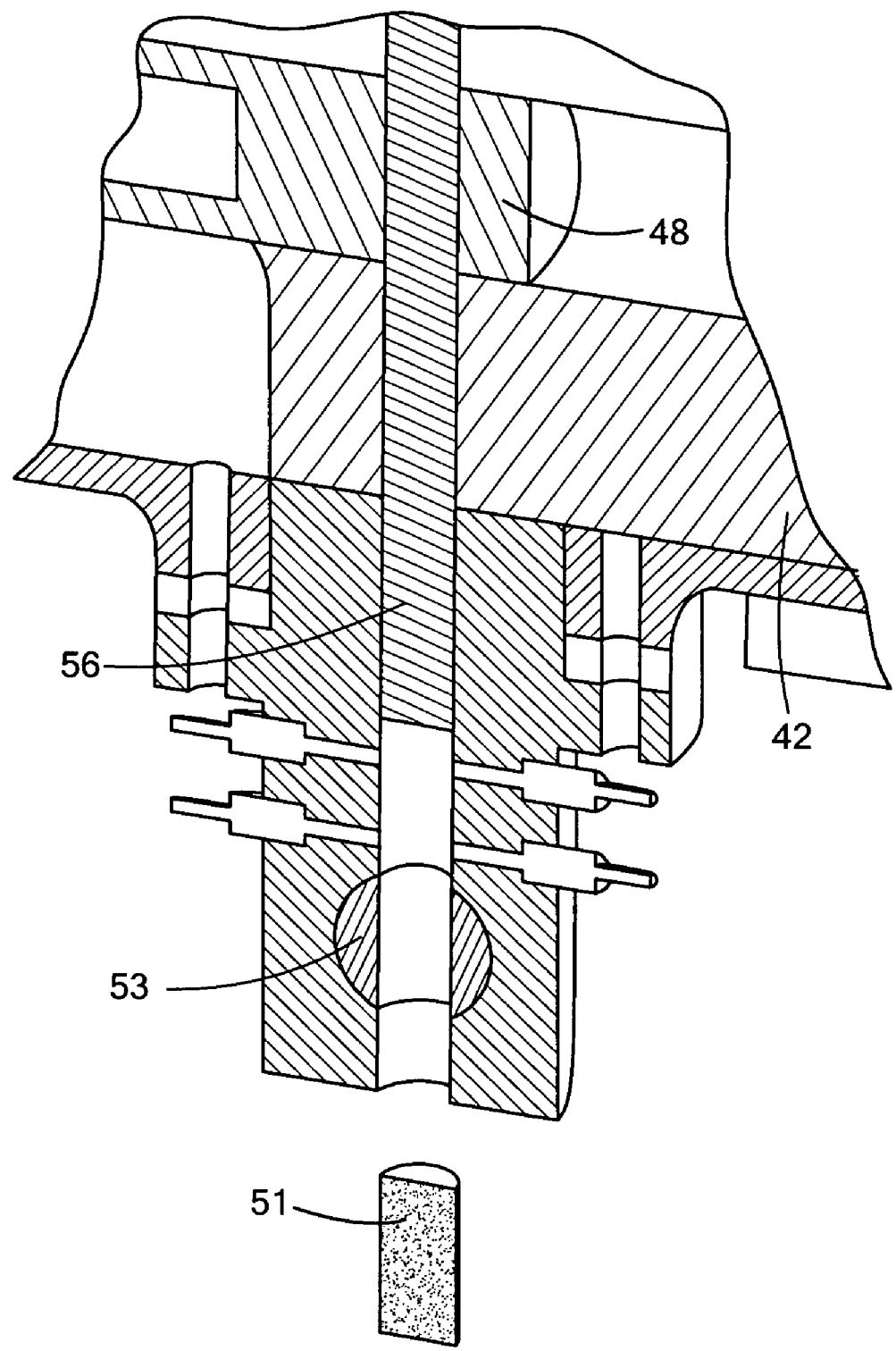

Pellet chamber 52, also outside the stack, is positioned beneath and is in communication with through hole 46 of cylinder 42. Ram 56 is drivable through both cylinder through hole 46 and piston collection volume orifice 50 when piston 48 is retracted to produce a pellet 51 of fly-ash in pellet chamber 52, FIGS. 4B-4C. Typically, the pellet is then transferred via a transfer mechanism configured to transfer the pellet from extractor 30' to an analyzer. FIGS. 4D-4F show how pellet 51 is allowed to exit pellet chamber 52 via rotation of valve 53 (see valve controller 59, FIG. 4A, operated by controller 34, FIG. 2). Thus, valve 53 serves, in this specific example, as a transfer mechanism for transferring the collected fly-ash from the extractor to the analyzer. Pneumatically driven ram expels pellet 51 as shown in FIGS. 4E-4F.

Figure 5:
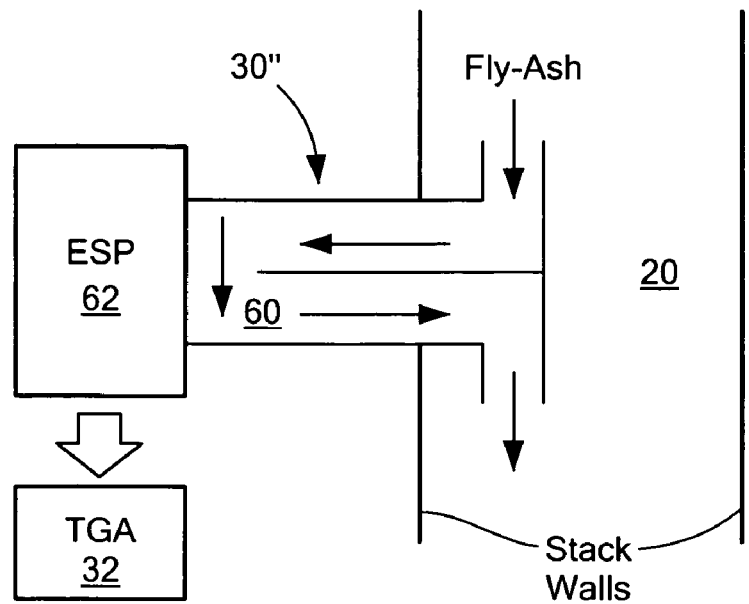
FIG. 5 is a schematic cross-sectional view showing a different version of an extractor.
Figure 6:
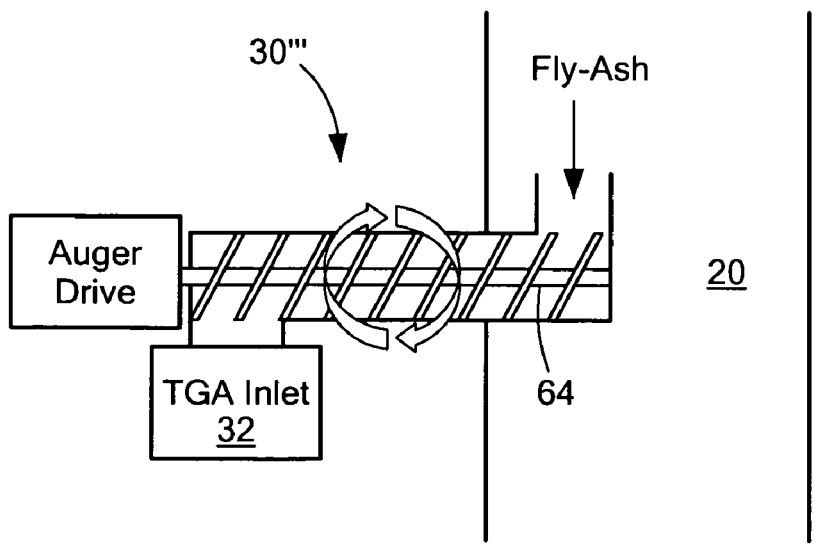
FIG. 6 is a schematic cross-sectional view showing still another example of a fly-ash sample extractor.

In another embodiment, extractor 30", FIG. 5 includes an electro-static precipitator. Air duct 60 redirects a small volume of gas/fly-ash exhaust mixture from stack 20 towards electrostatic precipitator 62 which gathers fly-ash on charged plates. These plates are subsequently passed through analyzer 32 for analysis. In another embodiment, extractor 30''', FIG. 6 includes motor driven rotary auger 64 used to compress and drive the fly-ash into the inlet of analyzer 32. Other extractors are possible, for example cyclone type devices, conveyors, and the like. And, bottom ash rather than fly-ash may be extracted and analyzed.

Figure 7:
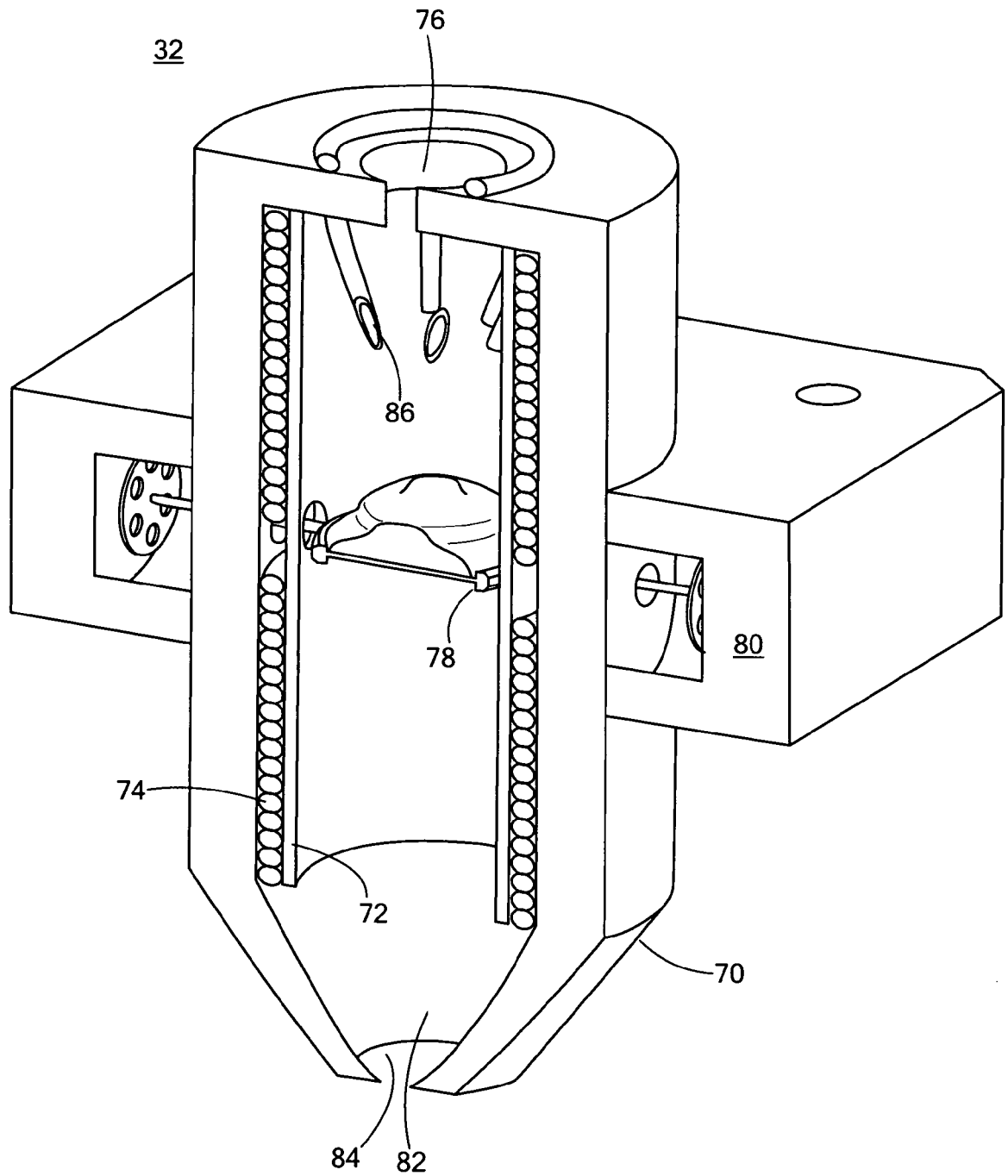
FIG. 7 is a schematic three-dimensional partially cross-sectional view showing an example of a thermal gravimetric analyzer useful in accordance with the system and method of the invention.

In one example, thermal gravimetric analyzer 32, FIG. 7 is configured to weigh the fly-ash, burn the fly-ash, and then weigh the fly-ash again to determine LOI data. Analyzer 32 includes insulated housing 70 with inner sleeve 72 and heating coils 74. A fly-ash sample, delivered from the extractor via a transfer mechanism, enters port 76 and is then positioned on resonator platform 78 where it is weighed by determining the resonant frequency of the platform/sample combination via electro-magnetic controls/actuator subsystem 80 or by a piezo, micro, or other balance. The temperature of chamber 82 is then increased via heating coils 74 to burn the fly-ash sample. The sample is then weighed again. The difference in weight before and after burning is used by controlling electronics 34, FIG. 2, (typically including an appropriately programmed processor) to determine the LOI data. Thereafter, actuator system 80, FIG. 7 flips resonator platform 78, 90° and the burned fly-ash exits the analyzer via exit port 84. Purge jets 86 are controlled by system 80 to purge any remaining fly-ash from chamber 82 and/or resonator platform 78. The heating chamber may be maintained at a constant temperature (approximately 800° C.) throughout the sampling process. The fly-ash is dropped onto the weighing platform, weighed and quickly combusted. Once the burn is complete, the sample is purged from the chamber via nitrogen gas exiting purged jets 86 and the system is ready for the next sample.

Figure 8:
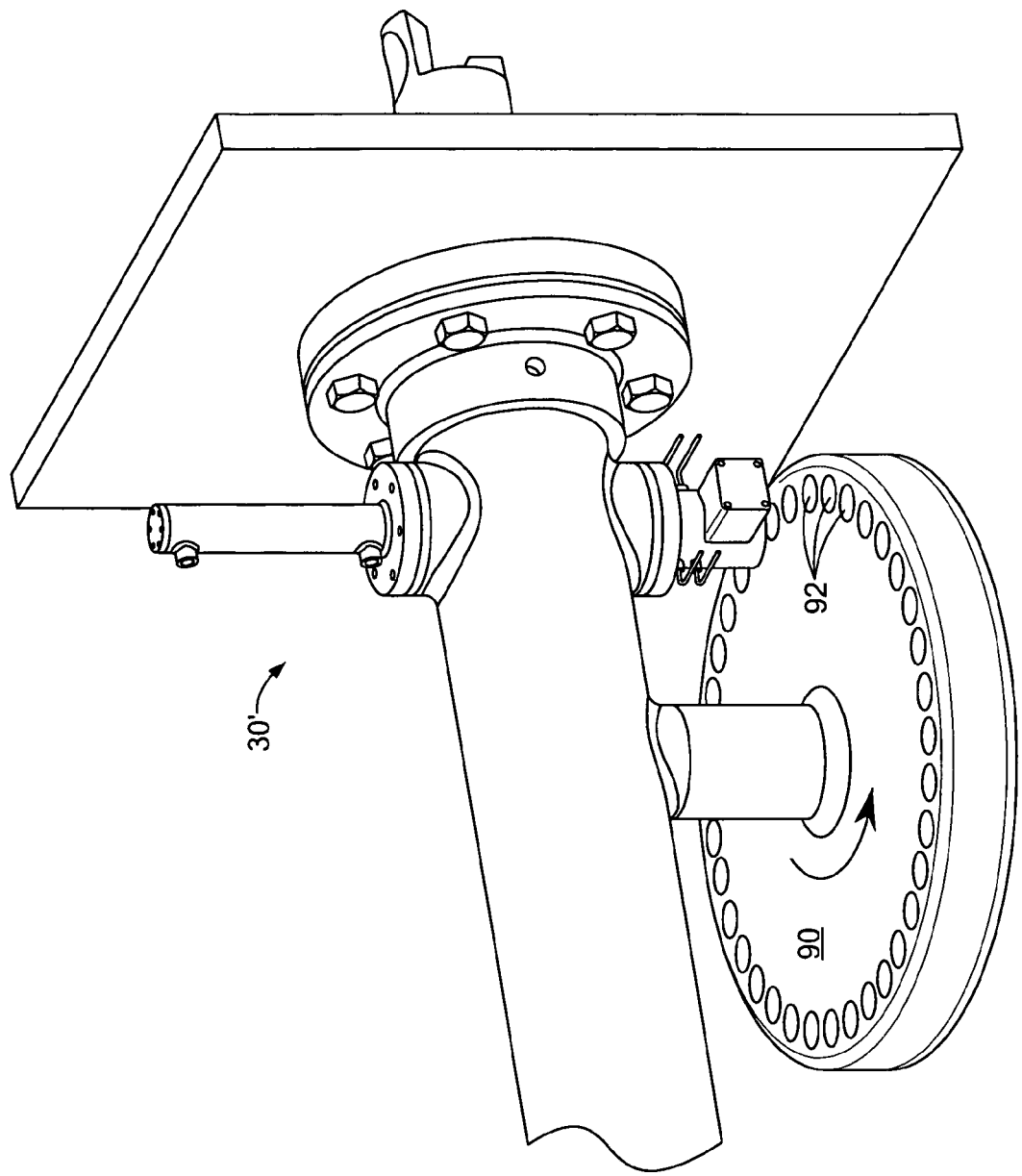
FIG. 8 is a schematic three-dimensional view showing how the extractor of FIG. 3 interfaces with the carousel input of a commercially available analyzer.

In another embodiment, a thermal gravimetric analyzer available from PerkinElmer, Inc. (Waltham, Mass.) is used, e.g., the STA 6000 Simultaneous Thermal Analyzer with an auto sampler. FIG. 8, for example, shows extractor 30', FIGS. 3-4, positioned above the input carousel 90 of such an analyzer with fly-ash pellet receptacles 92. Carousel 90 rotates to receive fly-ash pellets (see pellet 51, FIG. 4F) under the control of controller 34, FIG. 2.

The analyzer may be coupled directly to the extractor (and fed fly-ash by gravity, for example, or via an auger or the like) or may receive fly-ash from the extractor via a transfer mechanism. The fly-ash can be in pellet form or in powder form. A pellet of fly-ash may be easier to transfer, but it may also be more difficult to weigh and burn. The powder form of the fly-ash, although easier to burn, may be more difficult to transport and may require other steps taken to clean the extractor, the transfer mechanism, and the analyzer. Other type of analyzers can be used, for example, conductivity and spectrographic analyzers.

Figure 9:
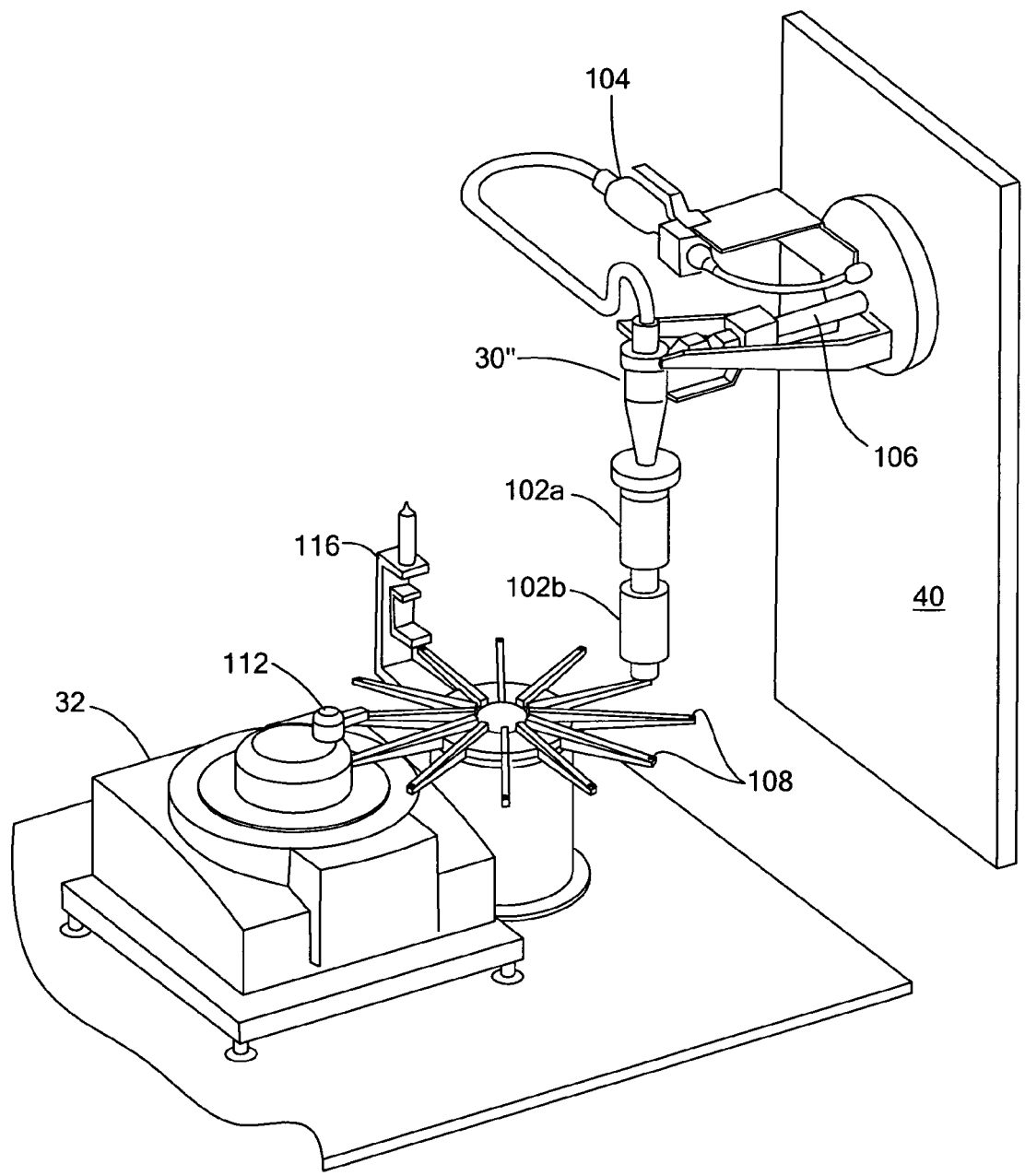
FIG. 9 is a schematic three-dimensional view of another LOI measurement system in accordance with the invention.

In another version, cyclone extractor 30", FIG. 9, with dispensing valves 102a and 102b coupled thereto is operated via vacuum generator 104 to both extract ash and purge (clean) the extractor. A conduit 106 through duct wall 40 is used to connect the interior of the duct to cyclone 30". Dispensing valves 102a and 102b are used to deposit a fly-ash sample in the wells 108 of transfer mechanism 110, in this example, a material handling carousel. Pick and place mechanism 112 of TGA 32 retrieves an ash sample from the wells of handler 110 and presents the ash sample to TGA 32 for analysis. Cleaning station 116 can be used to clean the ash out of wells 108 of handler 110 by a vacuum or purging action. In another example, a TGA is disposed directly below valve 102b which serves as the transfer mechanism.

Figure 10:
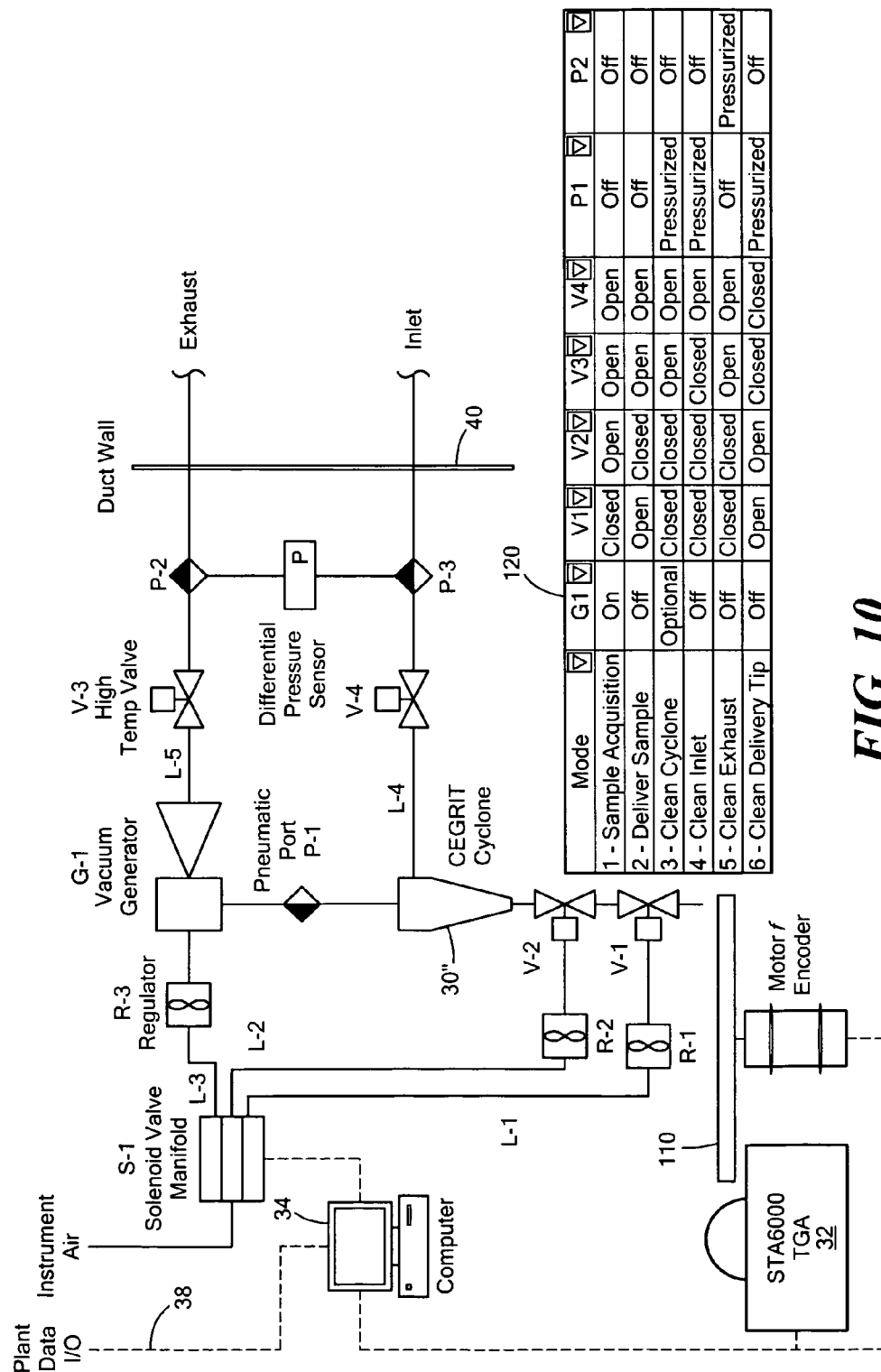
FIG. 10 is a block diagram showing the principle components of a more complete LOI measurement system in accordance with the invention.

FIG. 10 shows cyclone extractor 30", handler 110 and TGA 32 along with the valving and control lines used to operate the system. Table 120 delineates the operation of the system during sample acquisition, sample delivery, cleaning, and the like.

Figure 11:
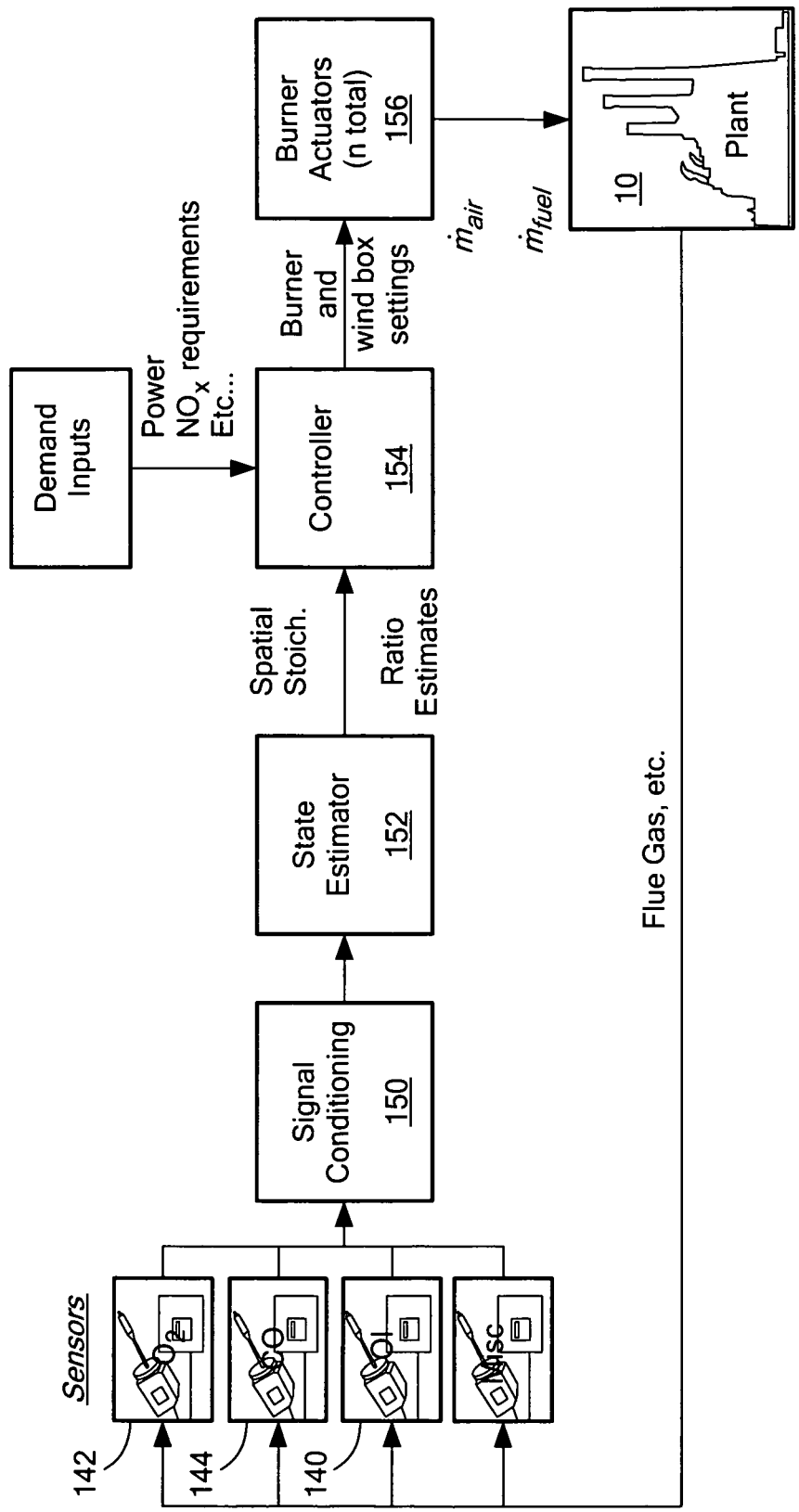
FIG. 11 is a block diagram showing how a LOT measurement system in accordance with the subject invention can be used for combustion process monitoring and control.

FIG. 11 illustrates how a LOI measurement system 140 can be used with other plant sensors such as oxygen sensor 142, carbon monoxide sensor 144, and the like to control various plant parameters via signal conditioning electronics 150, state estimator 152, and controller 154. In this example, plant burner actuators 156 are controlled by controller 154.

Preferably, the number of moving parts is minimized so that maintenance is not an issue. Also, it is preferred that the complete system is self-cleaning. As noted above, some analyzers employ carousels in which case the transfer mechanism is engineered to provide an interface between the extractor and the carousel of the analyzer.

In other embodiments, coal is analyzed before it is burned in the plant burners. In still other examples, other types of hydrocarbon fuels and/or bi-products of combustion are extracted and analyzed.

The preferred result, in one preferred embodiment, is a system and method for measuring loss-on-ignition directly, on-site, continuously, automatically, and without the need for excessive calibration.

Figure 12:
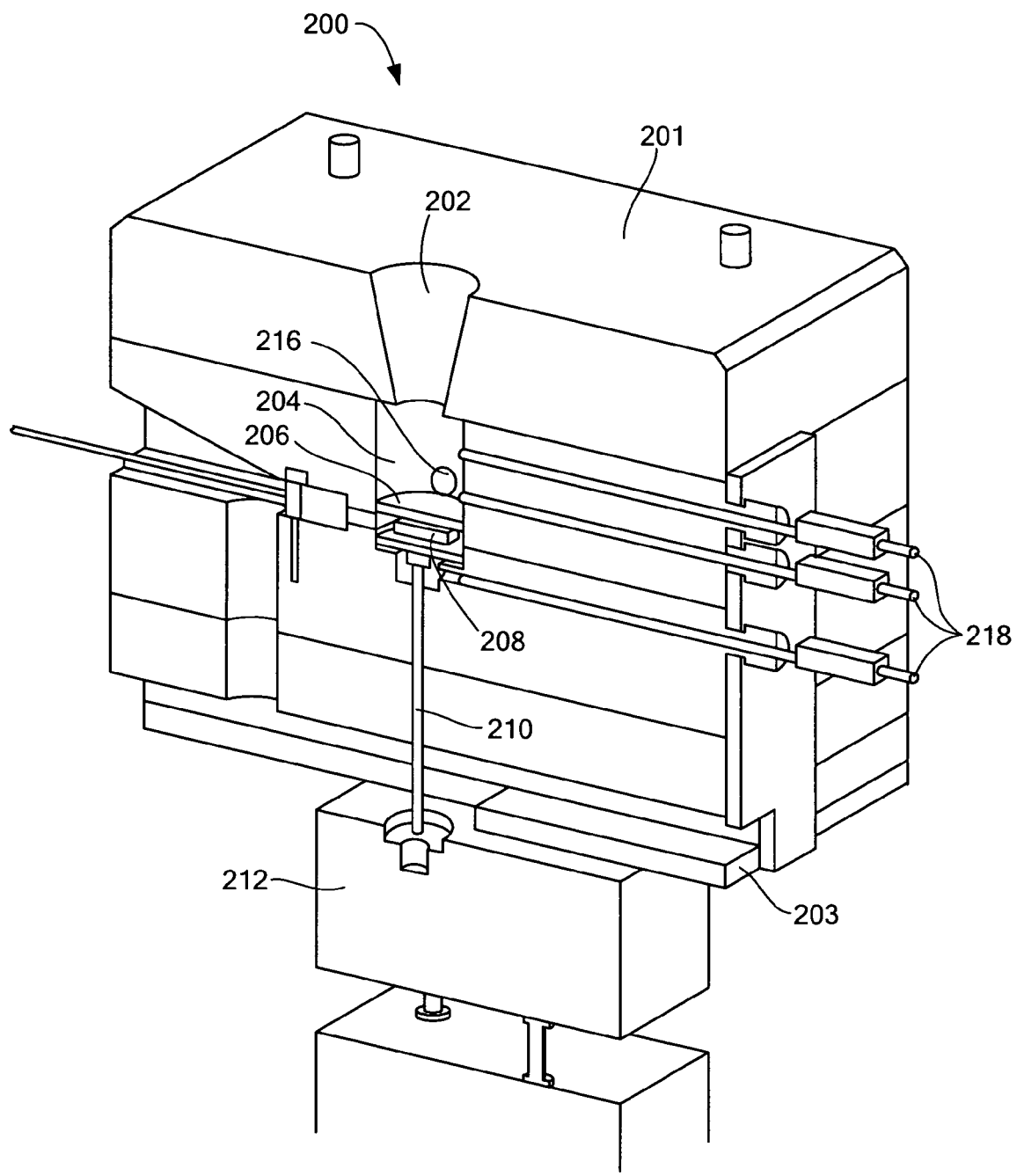
FIG. 12 is a schematic cross sectional view showing an example of an analyzer useful in accordance with the subject invention.
Figure 13:
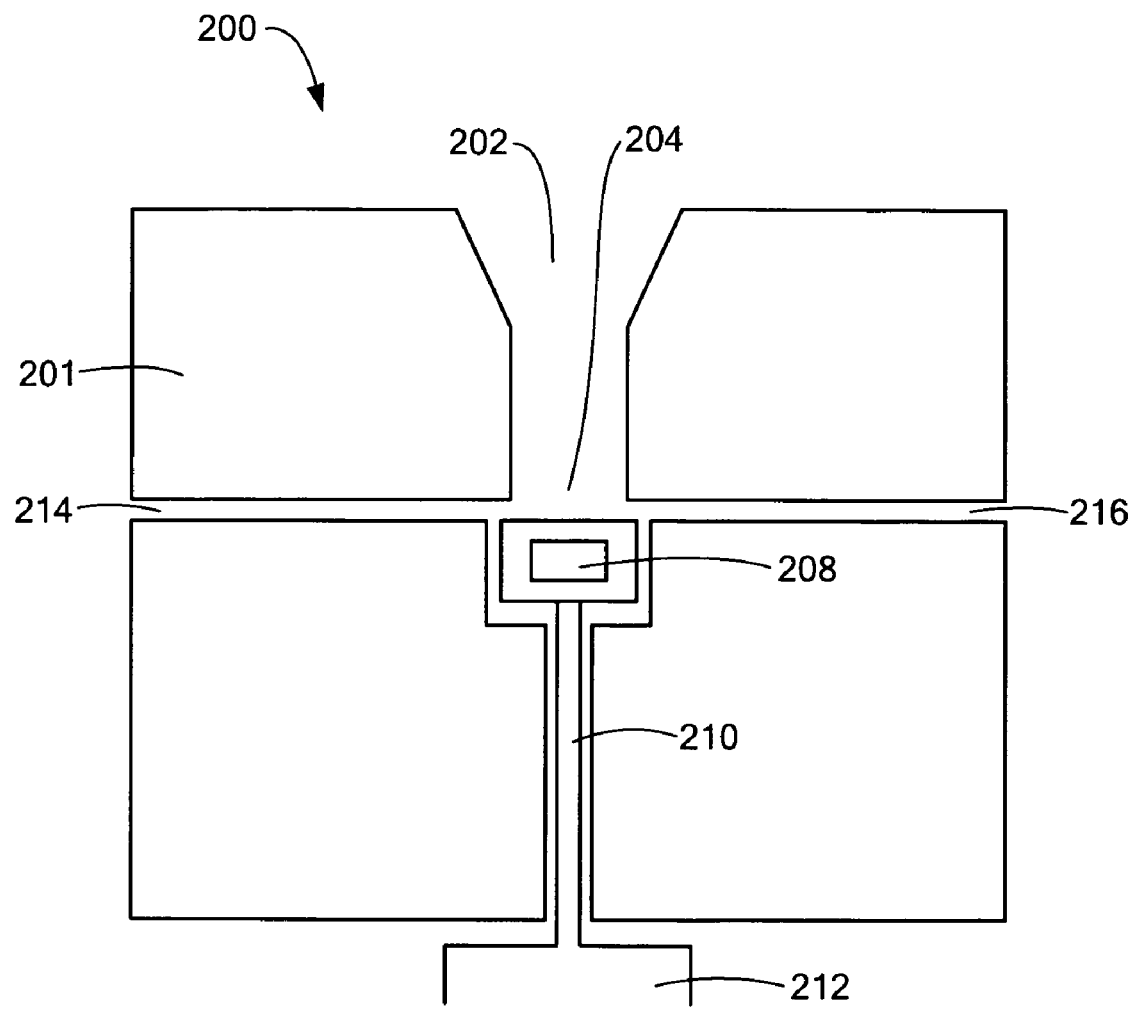
FIG. 13 is a schematic cross sectional view of the analyzer shown in FIG. 12.

FIGS. 12-13 show an example where analyzer 200 includes sample inlet 202 opening into chamber 204 within oven 201 supported by surface 203. Platen 206 is supported in chamber 204 by rod 210 coupled to balance 212. Ceramic heater 208 is located within platen 206. Thermocouples 218 may also be provided for monitoring the temperature of chamber 204. Chamber 204 also includes purge inlet 214 and purge outlet 216. Gas under pressure, optionally in combination with a vacuum source, is used to purge chamber 204 and clean platen 206.

Figure 14:
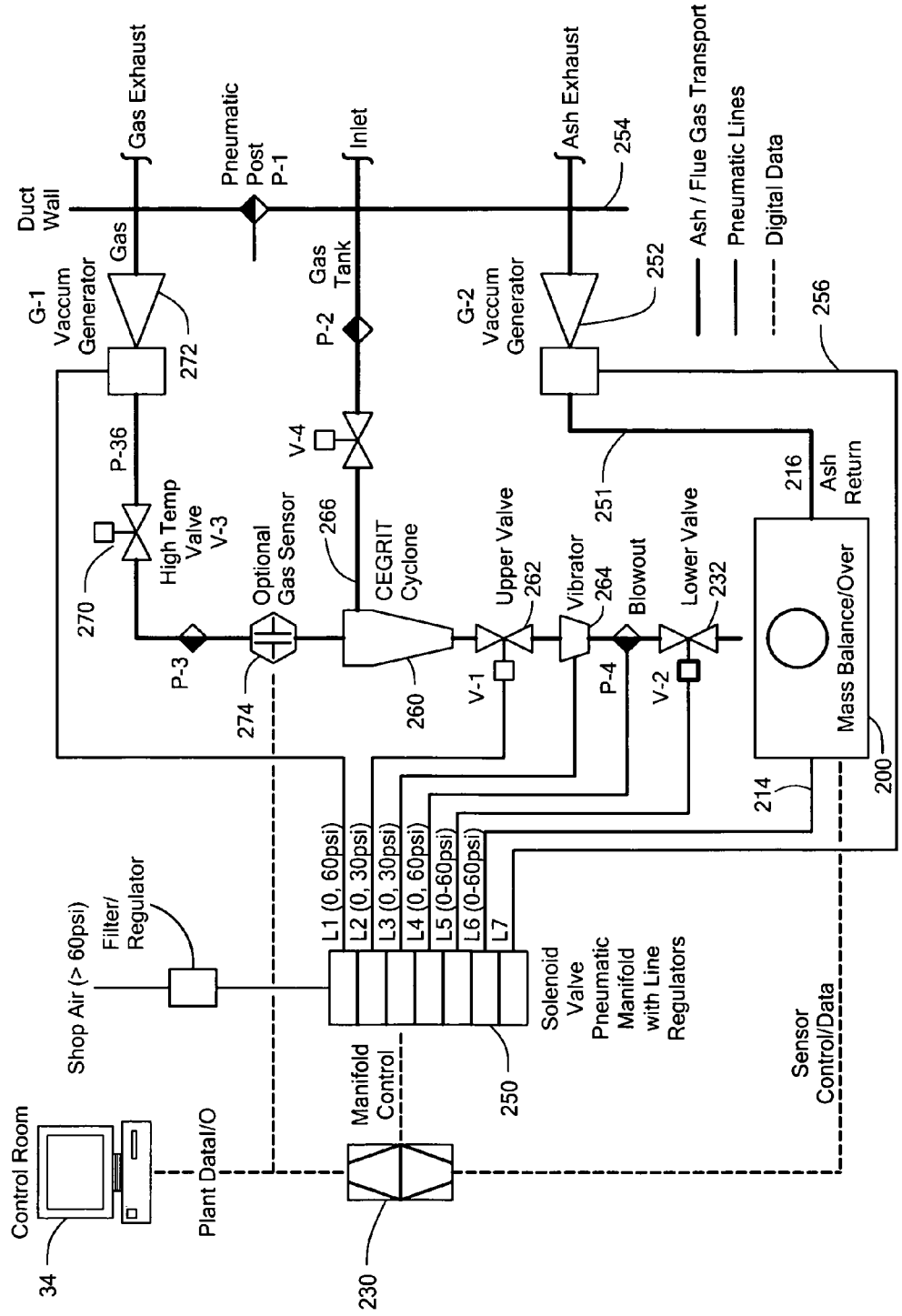
FIG. 14 is a block diagram showing the primary components associated with a complete in-line loss-on-ignition measurement system in accordance with one example of the invention.
Figure 15:
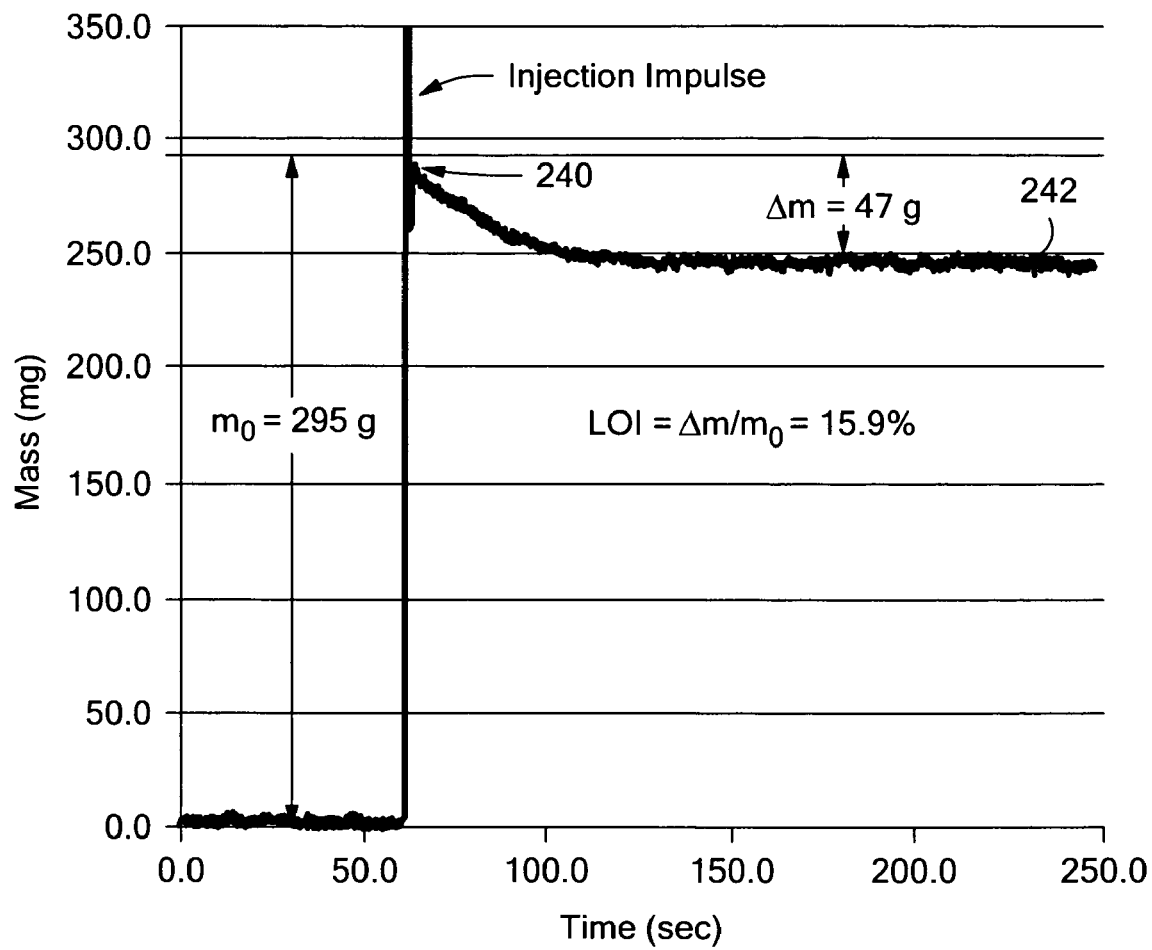
FIG. 15 is graph showing how the system of FIG. 14 determine loss on ignition data.

Controller 230, FIG. 14 is configured to actuate value 232 to open and dispense fly ash through oven inlet 202, FIG. 12 and onto platen 206. The controller then reads the weight ($m_o$) of the fly ash as an output from balance 212 as shown at 240 in FIG. 15. The controller then energizes ceramic heater 208, FIGS. 12-13 and the ash is burned. The controller then again reads the weight of the fly ash as an output from balance 212 at shown at 242 in FIG. 15 and calculates the difference in weight ($\Delta m$). The controller calculates the loss on ignition data as:

$$LOI = \frac{\Delta m}{m_0} \qquad (1)$$

Finally, controller 230, FIG. 14 actuates valve 250 to deliver gas through inlet 214 and out outlet 216 to clean platen 206, FIG. 13 and purge chamber 204 of any burned fly ash which is delivered, via line 251 and vacuum generator 252, also controller by controller 230 via pneumatic line 256, to exhaust stack 254. This whole process typically takes less than six minutes. The LOI percentage may be determined by fitting a curve to the mass profile of the burn process enabling the system to extrapolate or interpolate values for errant or missing data points. In particular this includes the period during and immediately after sample deposition when the balance is settling out, extrapolating the end of the burn profile so the burn does not have to continue through its entire course, and during other periods where disturbances may impact raw data quality.

The ash is preferably deposited and removed from the oven near operational temperatures through ports so the oven does not have to cycle through heating and cool-down periods. In other words, the LOI sample is dropped directly into a hot oven and it is removed without cooling the oven down. Minor temperatures variations may occur, but the system does not have to go through the lengthy temperature cycling common to TGA instruments and other burn processes.

In this particular example, the extractor subsystem includes cyclone 260, FIG. 14, valve 262, vibrator 264, and valve 232. Cyclone 260 is connected to exhaust stack 254 via line 266 and delivers fly ash to upper valve 262 while lower valve 232 delivers fly ash to analyzer 200. After valve 232 is closed by controller 230, valve 262 is opened to again deliver fly ash to valve 232. In this way, fly ash is always readily available for analyzing.

Gas extracted via cyclone 260 from the stack is delivered back to the stack via valve 270 and vacuum generator 272 (also controlled by controller 230 via valve 250). One or more gas sensors 274 may be provided to provide signals to controller 230 regarding the exhaust stack gases.

Advantages of the system described with respect to FIGS. 12-15 include the option of integrated 02 and CO as well as other gas sensors. Since the ash sample is delivered to the hot oven directly, there is no need for a warm up or cool down cycle and oven 200, FIGS. 12-13 can be temperature controlled to be at or around the ignition temperature of the ash. Balance 212 is exterior to the oven to limit the amount of heat applied to balance 212. Analyzing of the ash can occur fairly quickly and reliably because there are few moving parts. Cost is reduced and accuracy can be increased.

Although specific features of the invention are shown in some drawings and not in others, this is for convenience only as each feature may be combined with any or all of the other features in accordance with the invention. Also, the words "including", "comprising", "having", and "with" as used herein are to be interpreted broadly and comprehensively and are not limited to any physical interconnection. Moreover, any embodiments disclosed in the subject application are not to be taken as the only possible embodiments.

In addition, any amendment presented during the prosecution of the patent application for this patent is not a disclaimer of any claim element presented in the application as filed: those skilled in the art cannot reasonably be expected to draft a claim that would literally encompass all possible equivalents, many equivalents will be unforeseeable at the time of the amendment and are beyond a fair interpretation of what is to be surrendered (if anything), the rationale underlying the amendment may bear no more than a tangential relation to many equivalents, and/or there are many other reasons the applicant can not be expected to describe certain insubstantial substitutes for any claim element amended.

Other embodiments will occur to those skilled in the art and are within the following claims.

What is claimed is:

1. An in-line loss-on-ignition measurement system comprising:
    an on-site extractor subsystem configured to collect a fuel or a combustion by-product from a hydrocarbon fuel burning plant;
    an on-site analyzer coupled directly to the extractor subsystem and configured to receive the collected fuel or the combustion by-product from the extractor subsystem and configured to weigh and burn the collected fuel or the combustion by-product,
    the on-site analyzer including:
        a chamber,
        a platen positioned in the chamber and configured to support and burn the collected fuel or the combustion by-product,
        a heater disposed within the platen and configured to heat the platen, and
        a balance connected to the platen; and
    a controller responsive to the on-site analyzer and configured to determine the loss-on-ignition for the plant based on the weight of the collected fuel or the combustion by-product before and after it is burned on the platen.

2. The system of claim 1 in which the extractor subsystem includes a cyclone device coupled to an exhaust stack of the plant and having an output connected to an input of the on-site analyzer via one or more valves.

3. The system of claim 1 further including a rod extending between the platen and the balance.

4. The system of claim 1 in which the chamber includes a purge inlet and a purge outlet for removing a burned collected fuel or a burned combustion by-product from the platen.

5. The system of claim 4 in which the purge outlet is connected to an exhaust stack of the plant.

6. The system of claim 5 further including a vacuum source between the purge outlet and the exhaust stack of the plant.

7. The system of claim 4 in which the controller is configured to read the weight of the collected fuel or the combustion by-product on the platen, actuate the heater to burn the collected fuel or the combustion by-product, read the weight of the burned collected fuel or the combustion by-product on the platen, and purge the platen via the purge inlet and the purge outlet.

8. The system of claim 1 in which the extractor subsystem includes a valve with an inlet receiving the collected fuel or the combustion by-product and an outlet for dispensing the collected fuel or the combustion by-product and the on-site analyzer includes a sample inlet disposed beneath the valve outlet, the sample inlet connected to the chamber.

9. The system of claim 1, in which the extractor subsystem includes an electro-static precipitator.

10. The system of claim 1, in which the extractor subsystem includes a pellet chamber having an output connected to an input of the analyzer.

11. The system of claim 1, in which the extractor subsystem includes a motor driven rotary auger.

* * * * *